(12) United States Patent
Sagehashi et al.

(10) Patent No.: US 6,699,238 B1
(45) Date of Patent: *Mar. 2, 2004

(54) LASER OPERATING SYSTEM

(75) Inventors: Hideo Sagehashi, Tokyo-to (JP); Katsuhiko Kobayashi, Tokyo-to (JP); Masayuki Momiuchi, Tokyo-to (JP)

(73) Assignee: Kabushiki Kaisha Topcon, Tokyo-to (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/614,780

(22) Filed: Jul. 12, 2000

(30) Foreign Application Priority Data

Jul. 23, 1999 (JP) .......................................... 11-208820

(51) Int. Cl.$^7$ ............................................... A61B 18/18
(52) U.S. Cl. ............................. 606/10; 606/11; 606/12; 606/16; 606/17
(58) Field of Search .................... 606/2, 4–6, 8–19; 607/88, 89; 351/201, 204–212

(56) References Cited

U.S. PATENT DOCUMENTS

| | | | | |
|---|---|---|---|---|
| 4,881,808 A | * | 11/1989 | Bille et al. .................. 351/221 |
| 4,931,053 A | * | 6/1990 | L'Esperance, Jr. ............. 606/2 |
| 5,226,903 A | * | 7/1993 | Mizuno ........................ 606/17 |
| 5,634,920 A | * | 6/1997 | Hohla ......................... 606/12 |
| 6,099,522 A | * | 8/2000 | Knopp et al. ................. 606/10 |
| 6,217,570 B1 | * | 4/2001 | Nevyas ........................ 606/5 |

* cited by examiner

*Primary Examiner*—Roy D. Gibson
*Assistant Examiner*—A M Farah
(74) *Attorney, Agent, or Firm*—Nields & Lemack

(57) ABSTRACT

A laser operating system, comprising treatment laser beam projector for projecting a treatment laser beam to an affected site to be treated, sighting laser beam projector for projecting a sighting laser beam for aligning the treatment laser beam to the affected site, and an adjuster 36 for adjusting a spot diameter of the treatment laser beam, wherein output of the sighting laser beam projector is adjusted in association with adjusting operation of the adjuster.

4 Claims, 5 Drawing Sheets

LASER OPERATING SYSTEM

BACKGROUND OF THE INVENTION

The present invention relates to a laser operating system for performing surgical operation by projecting a laser beam for treatment, and in particular to a laser operating system for adequately and automatically adjusting brightness of a sighting laser beam to align the laser beam for treatment to an affected site to be treated.

In a laser operating system for medical use, a sighting laser beam is projected for adequately aligning a laser beam for treatment to an affected site to be treated, and the treatment laser beam is aligned by the sighting laser beam.

In general, the laser beam is guided via an optical fiber and a delivery optical system and is projected toward the affected site. A system shown in FIG. 5 is used as the delivery optical system for the laser beam.

In FIG. 5, reference numeral 1 indicates a dichroic mirror. At positions facing to the dichroic mirror 1, a treatment laser oscillator 2 and a sighting laser oscillator 3 are provided. The treatment laser beam 4 emitted from the treatment laser beam oscillator 2 passes through the dichroic mirror 1 and is projected to the affected site to be treated by the delivery optical system 6. A sighting laser beam 5 emitted from the sighting laser oscillator 3 is reflected by the dichroic mirror 1 and is then projected to the affected site by the delivery optical system 6.

The delivery optical system 6 is used to guide the laser beam to the affected site, and it comprises a condenser lens 7 for converging the treatment laser beam 4 and the sighting laser beam 5 to an incident end of the optical fiber, an optical fiber 8 for guiding the treatment laser beam 4 and the sighting laser beam 5, a first lens unit 9 for turning the laser beam projected from the optical fiber 8 to parallel beams, a second lens unit (zoom variable power mechanism) 10 for changing a focusing position and magnification of the laser beam, and a third lens unit 11 for focusing the laser beam.

In the delivery optical system 6 as described above, the affected site is specified by the sighting laser beam 5 projected from the sighting laser oscillator 3. When the affected site is specified, i.e. alignment is completed, the treatment laser beam 4 is projected to the affected site from the treatment laser oscillator 2. By high density thermal energy of the treatment laser beam 4, photocoagulation or incision is performed at the affected site. By moving the second lens unit 10 in the direction of the optical axis, a diameter of the spot of the laser beam at the projected position can be changed.

As described above, in the laser operating system of this type, the treatment laser beam and the sighting laser beam are projected coaxially via the same optical system. In this respect, when the spot diameter of the treatment laser beam is adjusted, the spot diameter of the sighting laser beam is also changed.

Even when the output of the sighting laser beam is adjusted by an operator at first so that the sighting can be performed with adequate brightness, if the spot diameter of the treatment laser beam is increased later, output of the sighting laser beam per unit area at the affected site (hereinafter referred as "output density") is decreased. As a result, the sighting laser beam is weakened and become dark, and it is difficult to see. On the contrary, when the spot diameter is set to a smaller value, the output density is increased. As a result, the sighting laser beam is too dazzling to see. For this reason, it has been necessary in the past for the operator to manually re-adjust the output of the sighting laser beam each time the spot diameter of the treatment laser beam is adjusted.

SUMMARY OF THE INVENTION

It is an object of the present invention to provide a laser operating system, by which it is possible, even when the setting of the spot diameter of the treatment laser beam is changed, to automatically adjust the output of the sighting laser beam in adequate manner in association with the change of setting and to perform sighting with adequate brightness at all times.

To attain the above object, the laser operating system according to the present invention comprises treatment laser beam projecting means for projecting a treatment laser beam to an affected site to be treated, sighting laser beam projecting means for projecting a sighting laser beam for aligning the treatment laser beam to the affected site, and adjusting means for adjusting a spot diameter of the treatment laser beam, wherein output of the sighting laser beam projecting means is adjusted in association with adjusting operation of the adjusting means. Also, the present invention provides the laser operating system as described above, wherein the output of the sighting laser beam projecting means is adjusted in such manner that output density of the sighting laser beam at the affected site is maintained approximately at constant level regardless of the adjusting operation of the spot diameter. Further, the present invention provides the laser operating system as described above, wherein output density of the sighting laser beam at the affected site is displayed. Also, the present invention provides the laser operating system as described above, wherein the output of the sighting laser beam is displayed. Further, the present invention provides the laser operating system as described above, wherein two modes can be selected, i.e. a mode without adjustment of associated operation and a mode with adjustment of associated operation.

DETAILED DESCRIPTION OF THE PREFERRED EMBODIMENT

Description will be given below on an embodiment of the present invention.

Figure 1:
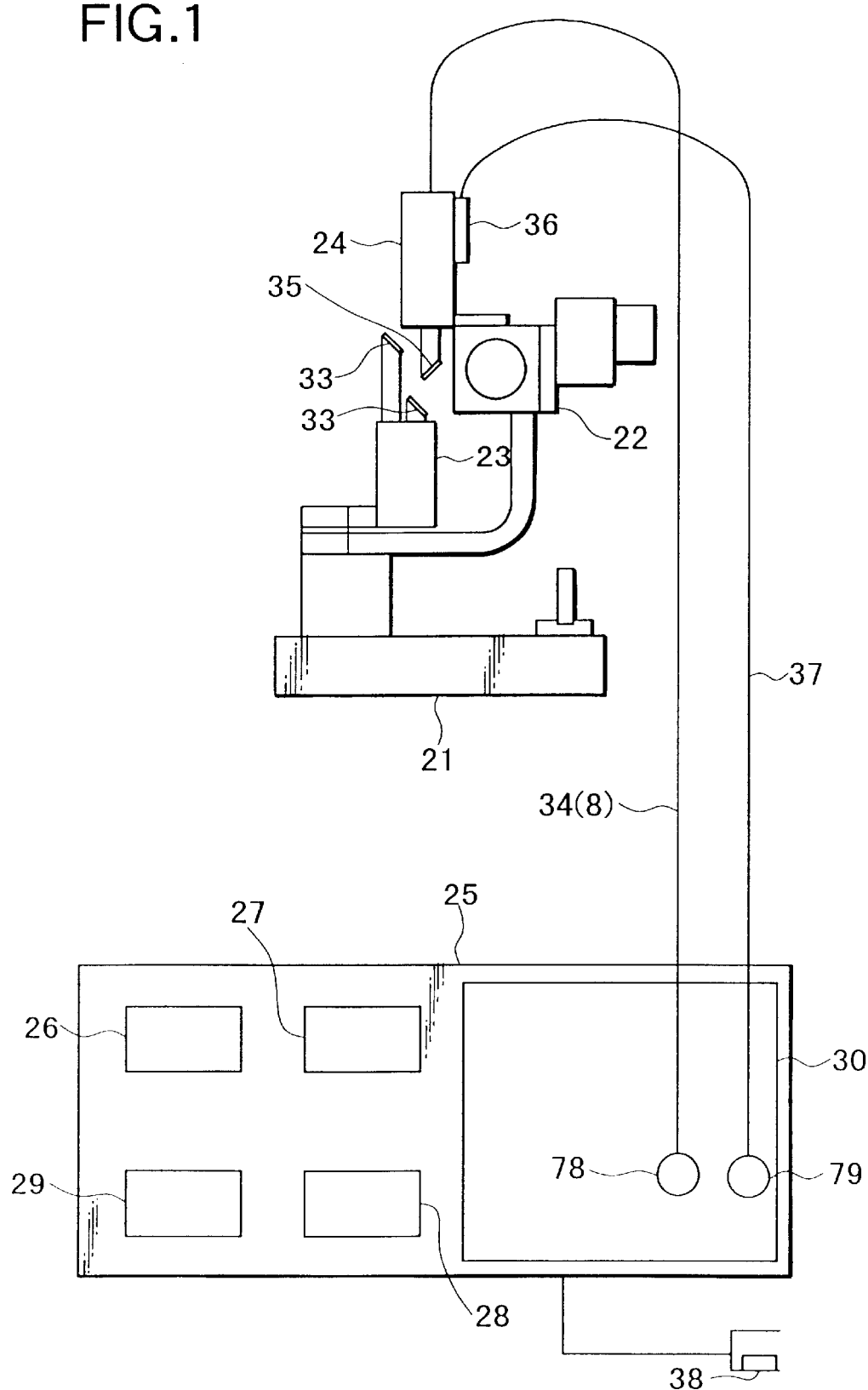
FIG. 1 is a schematical conceptual drawing of an embodiment of the present invention.

FIG. 1 is a drawing of a case where the present invention is applied on a laser operating system to be used for photocoagulation in ophthalmological treatment.

A base stand 21 is designed in such manner that its position can be adjusted with respect to an eye to be treated of a patient. A microscope unit 22 and an illuminating unit 23 are provided on the base stand 21, and a delivery unit 24 is arranged on the microscope unit 22.

A main unit 25 comprises a treatment laser beam oscillator 26 for emitting a treatment laser beam, a sighting laser beam oscillator 27 for emitting a sighting laser beam, an optical unit 28 for the treatment laser beam and the sighting laser beam, an electrical unit 29 containing a laser power source, a control unit, a control power unit, etc., and a control panel unit 30 having an operating switch, a display unit, etc.

The microscope unit 22 is used by an operator when it is necessary to examine an eye fundus in order to identify and specify an affected site to be treated. The illuminating unit 23 is provided with an illuminating light source (not shown), and it is used to illuminate the fundus of the eye to be treated by an illuminating light emitted from the illuminating light source via a reflection mirror 33.

The treatment laser beam and the sighting laser beam emitted from the treatment laser beam oscillator 26 and the sighting laser beam oscillator 27 are guided to the delivery unit 24 via the optical unit 28 and an optical fiber cable 34. The delivery unit 24 and the optical unit 28 have the same arrangement as those shown in FIG. 5. The optical fiber cable 34 is the same as the optical fiber 8 shown in FIG. 5.

Figure 5:
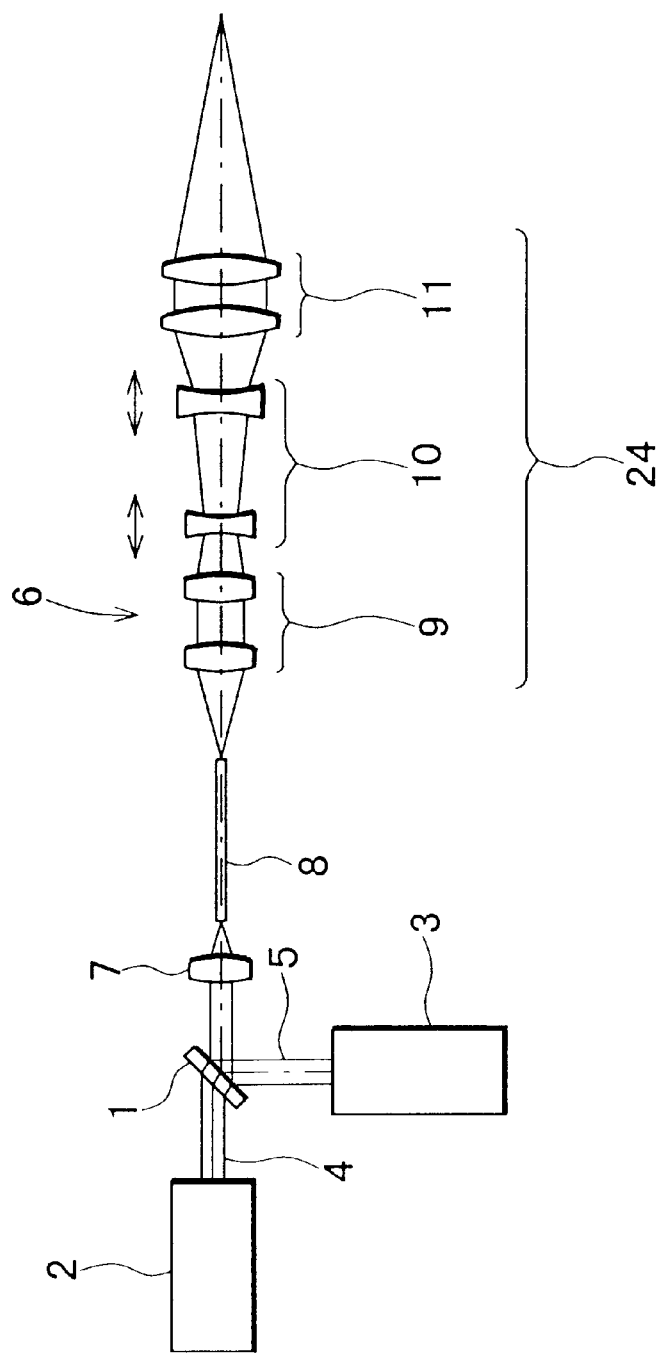
FIG. 5 is a schematic drawing of an optical unit in a conventional laser operating system.

The delivery unit 24 comprises an optical system (not shown) for focusing and guiding the treatment laser beam and the sighting laser beam to the affected site, and laser beam projecting spot diameter changing means for adjusting spot diameter at the projected position, e.g. a zoom variable power mechanism (shown by the second lens unit 10 in FIG. 5). After the conditions of the laser beams have been adjusted at the delivery unit 24, the treatment laser beam and the sighting laser beam are projected to the affected site of the eye to be treated via a reflection mirror 35. A spot diameter detector 36 is provided on the delivery unit 24 to detect the diameter of the spot of the projected treatment laser beam. The electric power to drive the zoom variable power mechanism of the delivery unit 24 and a zoom spot diameter detection signal from the spot diameter detector 36 are supplied or provided via an electric cable 37 connected to the electrical unit 29. In FIG. 1, reference numeral 38 indicates a foot switch to project or to stop projecting the treatment laser beam to the affected site.

Figure 2:
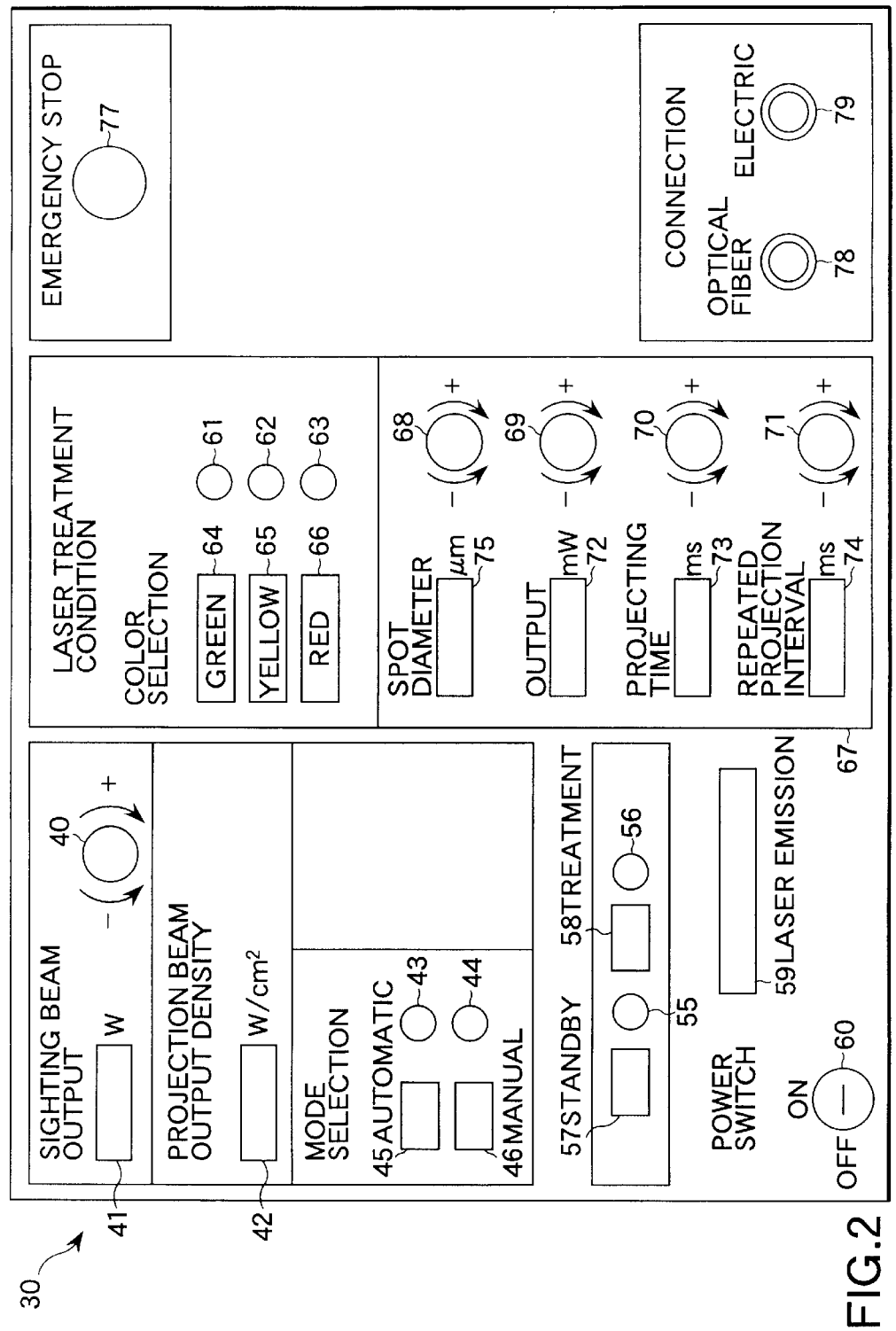
FIG. 2 is a drawing to explain a control panel unit of the embodiment of the present invention.

Referring to FIG. 2, description will be given now on general features of the control panel unit 30.

In this figure, reference numeral 40 represents a sighting laser beam output adjusting knob. Corresponding to the sighting laser beam output adjusting knob 40, a sighting laser beam output display unit 41 and a sighting laser beam output density display unit 42 are arranged. Reference numerals 43 and 44 represent an automatic mode selection switch and a manual mode selection switch respectively. There are further provided mode display units 45 and 46 respectively for displaying the modes selected by the automatic mode selection switch 43 and the manual mode selection switch 44. Reference numerals 55 and 56 represent switches for selecting operating conditions of the system respectively. The numeral 55 indicates a standby condition selection switch, and 56 shows a treatment condition selection switch. A standby condition display unit 57 and a treatment condition display unit 58 are provided corresponding to the standby condition selection switch 55 and the treatment condition selection switch 56 respectively. Reference numeral 59 represents a laser emission lamp, which is turned on when the laser beam is projected. Numeral 60 indicates a power switch.

In FIG. 2, reference numerals 61, 62 and 63 represent color selection switches, each being used to select one of green, yellow or red as the color of laser beam. Display units 64, 65 and 66 for displaying the selected laser beam color are provided corresponding to the color selection switches 61, 62 and 63 respectively.

In FIG. 2, reference numeral 67 represents a laser beam projecting condition setting unit. On this laser beam projecting condition setting unit 67, a spot diameter adjusting knob 68, an output adjusting knob 69, a projection time adjusting knob 70, and a repeated projection interval adjusting knob 71 are provided. Corresponding to these knobs 68, 69, 70 and 71, there are provided a spot diameter display unit 75, an output value display unit 72, a projection time display unit 73, and a repeated projection interval display unit 74. Numeral 77 is an emergency stop switch, 78 indicates a joining connector for connecting the optical fiber cable 34, and 79 shows a joining connector for connecting the electrical cable 37.

Figure 3:
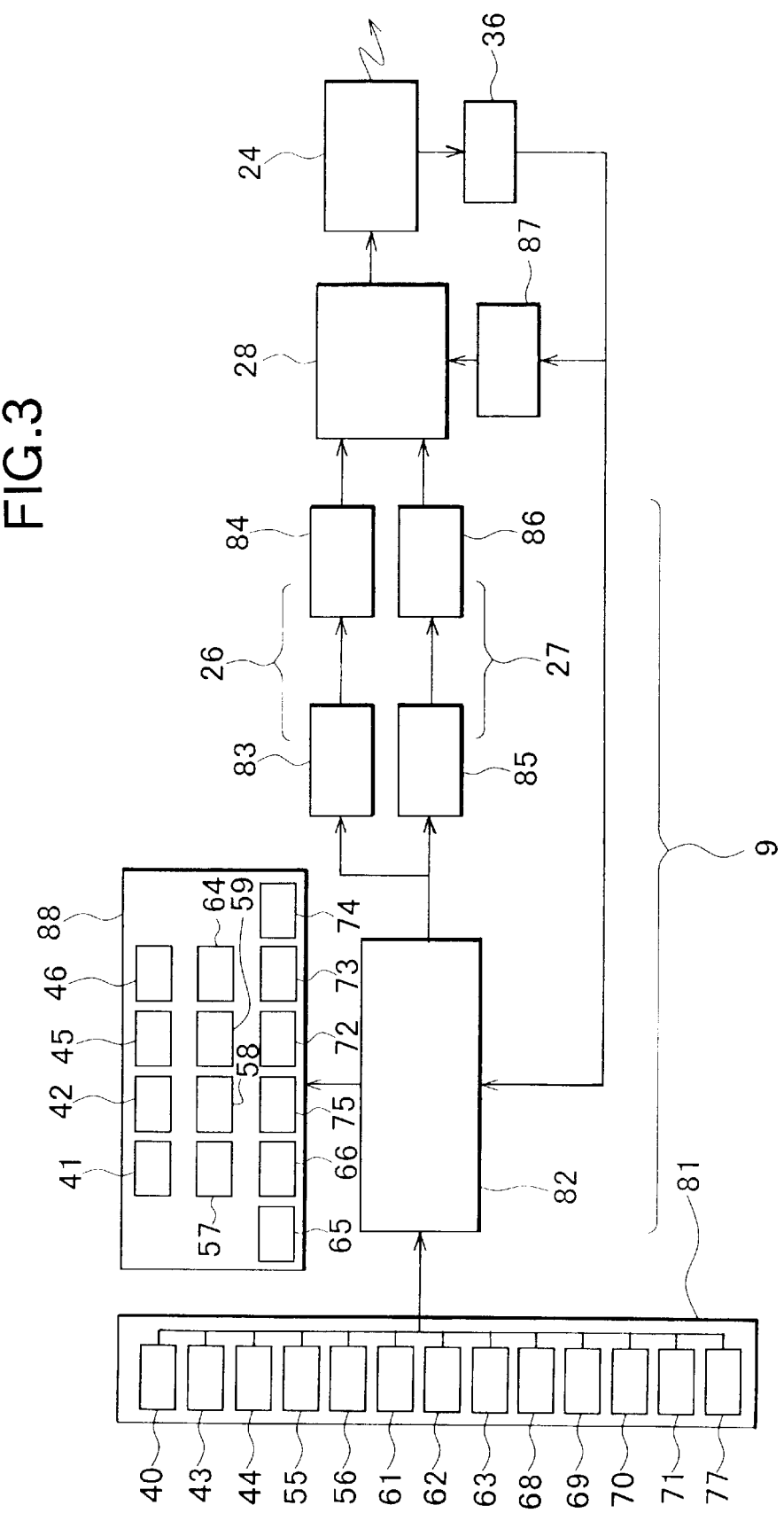
FIG. 3 is a block diagram showing a schematical arrangement of the embodiment of the present invention.

Referring to FIG. 3 and FIG. 5, description will be given now on general arrangement of the system.

An input unit 81 comprises various types of input means including the sighting laser beam output adjusting knob 40, the automatic mode selection switch 43, the manual mode selection switch 44, the standby condition selection switch 55, the treatment condition selection switch 56, the color selection switches 61, 62 and 63, the spot diameter adjusting knob 68, the output adjusting knob 69, the projection time adjusting knob 70, the repeated projection interval adjusting knob 71, and the emergency stop switch 77. An operation signal from the input unit 81 is inputted to a control unit 82. Based on the signal from the input unit 81, the control unit 82 adjusts an output condition of the sighting laser beam and controls a projecting condition of the treatment laser beam, an operating mode and an operating condition of the system, etc.

The control condition of the control unit 82 and the operating condition of the laser operating system are displayed on a display unit 88. The display unit 88 comprises the sighting laser beam output display unit 41, the sighting laser beam output density display unit 42, the mode display units 45 and 46 for displaying automatic mode and manual mode, the standby condition display unit 57, the treatment condition display unit 58, the laser emission lamp 59, the display units 64, 65 and 66 for displaying the colors of the laser beam, the output value display unit 72, the projection time display unit 73, the repeated projection interval display unit 74, and the spot diameter display unit 75.

The control unit 82 drives the treatment laser beam oscillator 26 to match each of the preset projecting conditions. The treatment laser beam oscillator 26 comprises a treatment laser beam emission driving unit 83 and a treatment laser beam emitting light source 84. The treatment laser beam emitted from the treatment laser beam emitting source 84 is guided to the delivery unit 24 via the optical unit 28 and the optical fiber cable 34, and it is then reflected by the reflection mirror 35 and is projected to the affected site.

The sighting laser beam oscillator 27 comprises a sighting laser beam emission driving unit 85 and a sighting laser beam emitting light source 86. The control unit 82 drives the sighting laser beam oscillator 27 for aligning the treatment laser beam to the affected site. The sighting laser beam oscillator 27 comprises the sighting laser beam emission driving unit 85 and the sighting laser beam emitting light source 86. When driven by the sighting laser beam emission driving unit 85 and emitted from the sighting laser beam emitting light source 86, the sighting laser beam is guided to the delivery unit 24 via the optical unit 28 and the optical fiber cable 34 in the same manner as the treatment laser beam. It is then reflected by the reflection mirror 35 and is projected to the affected site and specifies the affected site.

The control unit 82 issues a signal for spot diameter setting as set by the spot diameter adjusting knob 68 to a spot diameter setting driving unit 87. Further, it drives the zoom variable power mechanism 10 of the delivery unit 24 via the electric cable 37 and changes the spot diameter. The delivery unit 24 has an optical system common to both the treatment laser beam and the sighting laser beam. Thus, when the spot diameter of the treatment laser beam has been changed, the spot diameter of the sighting laser beam is also changed.

The spot diameter is detected by the spot diameter detector 36, and the result of detection is fed back to the spot diameter setting driving unit 87 via the electric cable 37, and it is adjusted in such manner that the detected spot diameter is turned to a preset value as set by the spot diameter adjusting knob 68.

Figure 4:
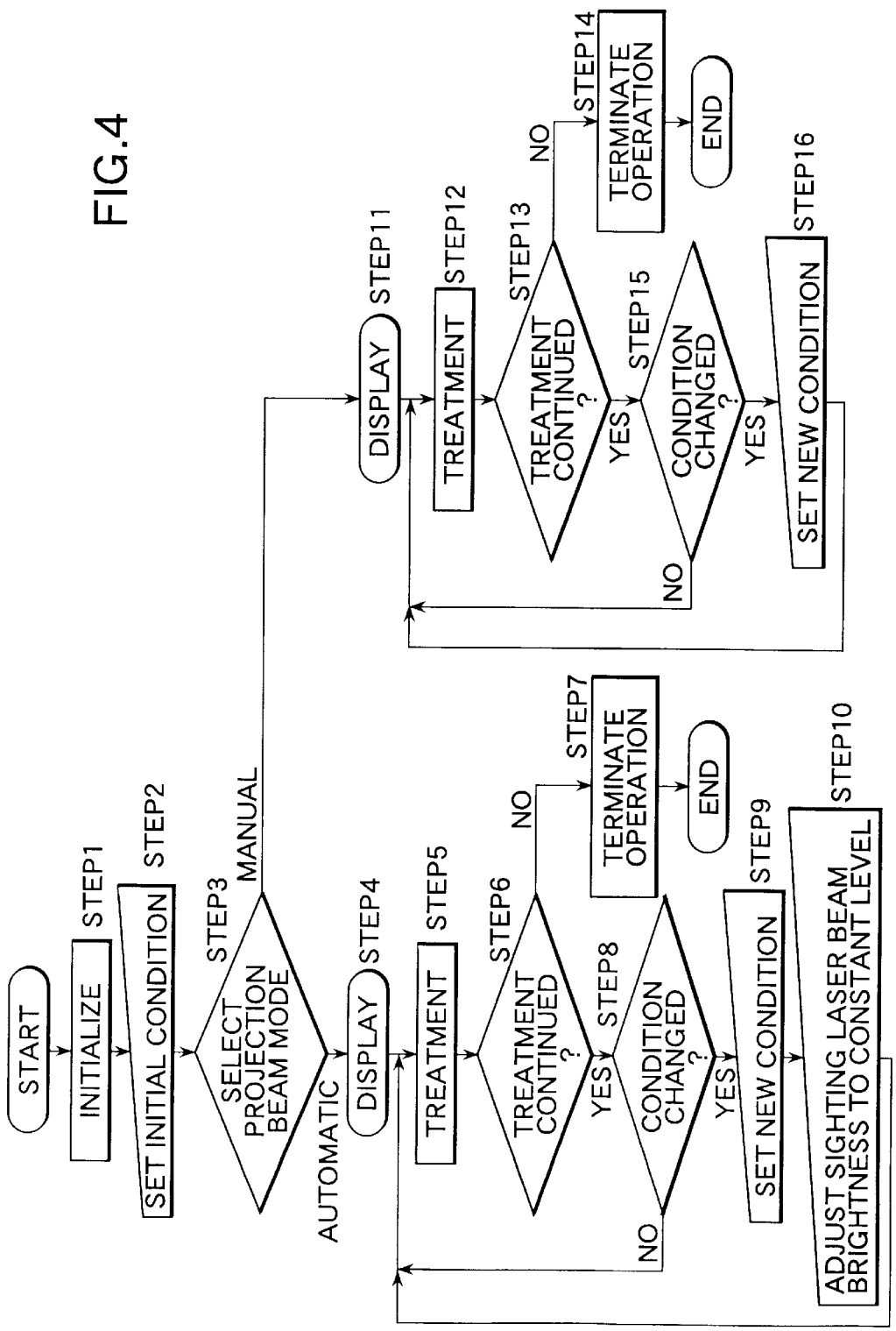
FIG. 4 is a flow chart showing operation of the embodiment of the present invention.

In the following, description will be given on operation referring to FIG. 4.

When electric power is supplied by turning the power switch 60 on, the system starts the operation.

Step 1: By a check program incorporated in advance in the system, abnormality is checked. If it is found abnormal, warning is issued to the operator by means such as display. If it is normal, initialization of the system is performed.

Step 2: After the initialization, a laser beam projecting condition is set. The spot diameter adjusting knob 68, the output adjusting knob 69, the projection time adjusting knob 70, and the repeated projection interval adjusting knob 71 are adjusted by the operator. One of the color selection switches 61, 62 or 63 is selected, and the projecting condition of the treatment laser beam is set. The sighting laser beam is projected, and it is checked whether the brightness is adequate (easy to see) or not. If the brightness is not adequate, the sighting laser beam output adjusting knob 40 is turned to adjust the brightness of the sighting laser beam.

Step 3: When the setting of the laser beam projecting condition has been completed, the automatic mode selection switch 43 or the manual mode selection switch 44 is operated to select the projecting mode of the sighting laser beam. When the automatic mode is selected, it is advanced to Step 4. If the manual mode is selected, it is advanced to Step 11.

Step 4: The laser beam projecting condition as set in advance and the selected mode are displayed on the display unit 88.

Step 5: By operating the treatment condition selection switch 56, it is turned to a condition ready for treatment. By operating the treatment condition selection switch 56, the treatment condition display unit 58 is turned on, and the condition ready for treatment is notified to the operator. The sighting laser beam is projected to the affected site. A projecting position of the treatment laser beam is determined. The foot switch 38 is pressed and the treatment laser beam is projected to the affected site, and treatment is performed.

Step 6: It is determined whether the treatment should be continued or not. When the treatment is terminated, it is advanced to Step 7.

Step 7: When it is judged that the treatment should be terminated, the standby condition selection switch 55 is operated, and it is turned to the standby condition. The standby condition display unit 57 is turned on, and it is notified to the operator that it is in the standby condition. The power switch 60 is turned off, and the operation of the system is terminated. The projection of the sighting laser beam is terminated, and the various types of display are turned off.

Step 8: When it is wanted to continue the treatment, it is turned back to Step 5 if there is no change in the treatment condition, and the treatment is continued. If there are changes in the treatment condition, the treatment condition is set again in Step 9.

Step 9: The wavelength (color) of the treatment laser beam is selected, and the treatment condition such as the change of the spot diameter is set again.

Step 10: In particular, when the spot diameter of the treatment laser beam is changed by the spot diameter adjusting knob 68, the spot diameter of the sighting laser beam is also changed at the same time.

The change of the spot diameter is detected by the spot diameter detector 36, and the result of detection is fed back to the control unit 82. Depending upon the amount of change of the spot diameter changed by the spot diameter adjusting knob 68, the control unit 82 controls the sighting laser beam emission driving unit 85. And the output of the sighting laser beam emitting light source 86 is increased or decreased so that the brightness of the sighting laser beam will be at adequate (constant) levels. As a result, by the adjustment using the spot diameter adjusting knob 68, the spot diameter is increased. With the increase of the spot diameter, the output of the sighting laser beam emitting light source 86 is automatically increased. If the spot diameter is set to a smaller value, the output of the sighting laser beam emitting light source 86 is automatically decreased in association with the setting. When the brightness of the sighting laser beam is adjusted to a constant level, it is turned back to Step 5, and the treatment is continued.

Step 11: When the manual mode is selected in the projection mode of the sighting laser beam, the preset operating condition and the selected mode are displayed on the display unit 88.

Step 12: By operating the treatment condition selection switch 56, it is turned to the condition ready for treatment. By operating the treatment condition selection switch 56, the treatment condition display unit 58 is turned on, and the condition ready for treatment is notified to the operator. The sighting laser beam is projected to the affected site, and the projecting position of the treatment laser beam is determined. The foot switch 38 is pressed. The treatment laser beam is projected to the affected site, and treatment is performed.

Step 13: It is determined whether the treatment should be continued or not. If the treatment is terminated, it is advanced to Step 14.

Step 14: When it is judged that the treatment should be terminated, the standby condition selection switch 55 is operated, and it is turned to the standby condition. The standby condition display unit 57 is turned on, and it is notified to the operator that it is the standby condition. The power switch 60 is turned off, and the operation of the system is terminated. The projection of the sighting laser beam is terminated, and the various types of display are turned off.

Step 15: When the treatment is continued, it is turned back to Step 12 if there is no change in the treatment condition, and the treatment is continued. If there are changes in the treatment condition, the treatment condition is set again in Step 16.

Step 16: The wavelength (color) of the treatment laser beam is selected and the treatment condition such as change of the spot diameter are set again. Here, the manual mode is selected. Even when the spot diameter is changed by the spot diameter adjusting knob 68, the output of the sighting laser beam emitting light source 86 is not automatically adjusted. In this case, the brightness of the sighting laser beam is changed in association with the change of the spot diameter. The brightness is adjusted by the sighting laser beam output adjusting knob 40. When the brightness of the sighting laser beam is adjusted, it is turned back to Step 12, and the treatment is continued.

According to the present invention, setting of the spot diameter of the treatment laser beam is changed in association with the change of the treatment condition. Even when the spot diameter of the sighting laser beam is changed in association with the change of the setting, the output of the sighting laser beam is automatically adjusted. As a result, collimation can be performed at adequate brightness at all times, and this extensively improves ease of operation in the adjustment.

What is claimed is:

1. A laser operating system, comprising treatment laser beam projecting means for projecting a treatment laser beam, sighting beam projecting means for projecting a sighting beam, a common delivery unit for projecting said treatment laser beam and sighting beam to an affected site, an optical means for guiding said treatment laser beam from said treatment laser beam projecting means and said sighting beam from said sighting beam projecting means to said delivery unit, said delivery unit comprising a spot diameter adjusting means, wherein said spot diameter adjusting means adjusts a spot diameter of said treatment laser beam to a required value, and the power of said sighting beam projecting means is adjusted in such a manner that the brightness of said sighting beam at said affected site is maintained approximately at a constant level regardless of said adjusting operation of said spot diameter.

2. A laser operating system according to claim 1, wherein the brightness of said sighting beam at said affected site is displayed.

3. A laser operating system according to claim 1, wherein said power of said sighting beam is displayed.

4. A laser operating system according to claim 1, wherein said power of said sighting beam projecting means is adjusted in association with said adjusting operation of said spot diameter adjusting means, and wherein two modes can be selected, a first mode without adjustment of said associated operation and a second mode with adjustment of said associated operation.

* * * * *